(12) United States Patent
Guskey et al.

(10) Patent No.: US 9,717,674 B1
(45) Date of Patent: Aug. 1, 2017

(54) SKIN CLEANSING COMPOSITIONS COMPRISING BIODEGRADABLE ABRASIVE PARTICLES

(71) Applicant: The Procter & Gamble Company, Cincinnati, OH (US)

(72) Inventors: Gerald John Guskey, Symmes Township, OH (US); Denis Alfred Gonzales, Brussels (BE); Karl Shiqing Wei, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/091,682

(22) Filed: Apr. 6, 2016

(51) Int. Cl.
| | |
|---|---|
| *A61Q 19/10* | (2006.01) |
| *A61K 8/81* | (2006.01) |
| *A61Q 17/04* | (2006.01) |
| *A61Q 19/08* | (2006.01) |
| *A61Q 19/04* | (2006.01) |
| *A61Q 19/02* | (2006.01) |
| *A61Q 15/00* | (2006.01) |
| *A61Q 5/00* | (2006.01) |
| *A61Q 19/00* | (2006.01) |
| *A61Q 19/06* | (2006.01) |

(52) U.S. Cl.
CPC ............ *A61K 8/8164* (2013.01); *A61Q 5/006* (2013.01); *A61Q 15/00* (2013.01); *A61Q 17/04* (2013.01); *A61Q 19/007* (2013.01); *A61Q 19/008* (2013.01); *A61Q 19/02* (2013.01); *A61Q 19/04* (2013.01); *A61Q 19/06* (2013.01); *A61Q 19/08* (2013.01); *A61Q 19/10* (2013.01); *A61K 2800/28* (2013.01); *A61K 2800/413* (2013.01); *A61K 2800/522* (2013.01)

(58) Field of Classification Search
None
See application file for complete search history.

(56) References Cited

U.S. PATENT DOCUMENTS

| | | |
|---|---|---|
| 6,699,963 B2 | 3/2004 | Noda et al. |
| 7,943,561 B1 | 5/2011 | Myers et al. |
| 8,008,242 B1 | 8/2011 | Imam et al. |
| 8,084,809 B2 | 12/2011 | Maeda et al. |
| 8,236,332 B2 | 8/2012 | Hedges |
| 8,546,318 B2 | 10/2013 | D'Ambrogio et al. |
| 8,613,956 B2 | 12/2013 | Kleiman et al. |
| 8,648,024 B2 | 2/2014 | Palla-Venkata et al. |

(Continued)

FOREIGN PATENT DOCUMENTS

| | | |
|---|---|---|
| EP | 2 338 962 A1 | 6/2011 |
| EP | 2 338 963 A1 | 6/2011 |

(Continued)

*Primary Examiner* — Isaac Shomer
(74) *Attorney, Agent, or Firm* — Betty J. Zea (57) ABSTRACT

A skin cleansing composition having biodegradable abrasive particles, is provided. The abrasive particles have a mean Circularity of from about 0.10 to about 0.60 and a mean particle size as expressed by the area-equivalent diameter of about 500 μm to about 2,000 μm and a Biodegradable Rate of about 30% to about 100%. The composition has a structured surfactant phase or surfactant phase having a Yield Stress of about 1 Pa to about 100 Pa or a Yield Stress of about 0.1 Pa to about 10 Pa, respectively.

18 Claims, 1 Drawing Sheet

(56) References Cited

U.S. PATENT DOCUMENTS

| | | | |
|---|---|---|---|
| 8,852,643 B2* | 10/2014 | Gonzales | A61Q 5/02 424/401 |
| 9,616,002 B2* | 4/2017 | Gonzales | A61K 8/0245 |
| 2004/0266645 A1 | 12/2004 | Albrecht et al. | |
| 2006/0079421 A1* | 4/2006 | Wagner | A61K 8/02 510/130 |
| 2008/0226580 A1 | 9/2008 | Maeda et al. | |
| 2009/0054286 A1 | 2/2009 | Schmit et al. | |
| 2009/0196836 A1* | 8/2009 | Tanner | A61K 8/03 514/1.1 |
| 2009/0318554 A1 | 12/2009 | Kleiman et al. | |
| 2010/0166844 A1 | 7/2010 | Mougin et al. | |
| 2010/0279909 A1 | 11/2010 | Boyke et al. | |
| 2011/0262371 A1 | 10/2011 | Deleersnyder et al. | |
| 2011/0287105 A1 | 11/2011 | Gittleman | |
| 2012/0009235 A1 | 1/2012 | Thilker et al. | |
| 2012/0009285 A1 | 1/2012 | Wei et al. | |
| 2012/0077880 A1 | 3/2012 | Quan et al. | |
| 2012/0077881 A1 | 3/2012 | Quan et al. | |
| 2012/0145172 A1 | 6/2012 | Shao et al. | |
| 2012/0178858 A1 | 7/2012 | Wnuk et al. | |
| 2012/0317736 A1 | 12/2012 | Gonzales et al. | |
| 2012/0321568 A1 | 12/2012 | Gonzales et al. | |
| 2012/0322713 A1 | 12/2012 | Perez-Prat Vinuesa et al. | |
| 2013/0039961 A1* | 2/2013 | Gonzales | A61K 8/8117 424/401 |
| 2013/0130963 A1* | 5/2013 | Perez-Prat Vinuesa | C11D 17/08 510/236 |
| 2013/0149273 A1 | 6/2013 | Wei et al. | |
| 2014/0026916 A1 | 1/2014 | Havens et al. | |
| 2014/0128306 A1 | 5/2014 | Miyata et al. | |
| 2014/0294965 A1 | 10/2014 | Brown et al. | |
| 2014/0352721 A1* | 12/2014 | Gonzales | C11D 17/0013 134/7 |
| 2015/0231042 A1 | 8/2015 | Gonzales et al. | |

FOREIGN PATENT DOCUMENTS

| | | |
|---|---|---|
| EP | 2 338 964 A2 | 6/2011 |
| EP | 2 338 965 A1 | 6/2011 |
| EP | 2 338 966 A1 | 6/2011 |
| EP | 2 431 452 A1 | 3/2012 |
| EP | 2 431 453 A1 | 3/2012 |
| EP | 2 431 454 A1 | 3/2012 |
| EP | 2 431 455 A1 | 3/2012 |
| EP | 2 631 286 A1 | 8/2013 |
| EP | 2 719 752 A1 | 4/2014 |
| EP | 2 808 379 A1 | 12/2014 |
| EP | 2 821 469 A1 | 1/2015 |
| EP | 2 821 472 A1 | 1/2015 |
| EP | 2 847 311 B1 | 4/2016 |
| FR | 2 964 663 A1 | 3/2012 |
| JP | 2004-26788 A | 1/2004 |
| JP | 2007-197602 A | 8/2007 |
| JP | 2000-26229 A | 1/2009 |
| JP | 4331294 B2 | 9/2009 |
| JP | 2010-270085 A | 12/2010 |
| JP | 2012-233057 A | 11/2012 |
| JP | 2012-233128 A | 11/2012 |
| JP | 2013-136732 A | 7/2013 |
| KR | 2009-0056295 A | 6/2009 |
| WO | 2004/043329 A2 | 5/2004 |
| WO | 2010/103215 A1 | 9/2010 |
| WO | 2011/079160 A2 | 6/2011 |
| WO | 2011/116963 A2 | 9/2011 |
| WO | 2011/128308 A1 | 10/2011 |
| WO | 2011/133438 A1 | 10/2011 |
| WO | 2011/133508 A1 | 10/2011 |
| WO | 2011/154508 A1 | 12/2011 |
| WO | 2012/167903 A2 | 12/2012 |
| WO | 2012/169518 A1 | 12/2012 |
| WO | 2012/177615 A1 | 12/2012 |
| WO | 2012/177617 A1 | 12/2012 |
| WO | 2012/177628 A1 | 12/2012 |
| WO | 2012/177676 A1 | 12/2012 |
| WO | 2012/177757 A2 | 12/2012 |
| WO | 2013/086251 A1 | 6/2013 |
| WO | 2013/170002 A1 | 11/2013 |
| WO | 2013/187917 A1 | 12/2013 |
| WO | 2013/187918 A1 | 12/2013 |
| WO | 2013/188626 A2 | 12/2013 |
| WO | 2014/193913 A1 | 12/2014 |
| WO | 2014/193920 A1 | 12/2014 |
| WO | 2016/004159 A1 | 1/2016 |
| WO | 2016/004160 A1 | 1/2016 |

\* cited by examiner

SKIN CLEANSING COMPOSITIONS COMPRISING BIODEGRADABLE ABRASIVE PARTICLES

FIELD OF THE INVENTION

The present invention relates to a skin cleansing composition comprising biodegradable abrasive particles, and methods of making and using the same.

BACKGROUND OF THE INVENTION

Skin cleansing compositions routinely include abrasive particles for a variety of reasons such as cleansing the skin (e.g., removal of dirt, sebum, or oil) or improving the appearance of the skin (e.g., exfoliation). Abrasive particles are commonly made from petroleum-based synthetic polymers like polystyrene or cross-linked styrene (XST) and/or polyurethane (PU), polyolefins, or waxes. Unfortunately, these petroleum-based synthetic polymers may pose long-term disposal problems and could have adverse effects on the environment.

Current market demands for more green alternatives, has led to a start in the use of biobased abrasive particles in fabric and home care products for cleaning dishes, clothes, and hard surfaces. Existing biodegradable abrasive particles that are designed for certain fields of application such as hard surface cleaning, detergents for dish or clothes, however, which require scouring of hard to remove stains on inanimate surfaces, are not generally appropriate to use on skin. These abrasive particles may be overly abrasive and may damage the skin.

Less aggressive biodegradable abrasive particles may, on the other hand, yield poor or inadequate cleansing performance as evidenced by soil or make-up remaining on the skin after use. Also in personal cleansing compositions it is desirable to have abrasive particles that are large enough to be seen and felt by the consumer, without having a gritty texture. Existing biodegradable abrasive particles, however, may have an undesirable gritty texture and may feel overly coarse. Formulators often must choose between visible, larger, but overly abrasive particles that may cause damage on the skin and gentler abrasive particles with a better sensorial feel but with inadequate cleansing efficacy and that cannot be seen by the user.

The use of biobased polymers as biodegradable abrasive particles, in skin cleansing compositions, particularly body wash cleansers, has only been minimally explored for optimal abrasive particle properties, optimal stability and optimal compatibility with other components in skin cleansing chassis. Skin cleansing compositions can be structured to suspend and stabilize dispersions of benefit agents and other materials, while maintaining physical integrity of the personal care compositions.

Structured surfactants are a useful way to provide structure. These surfactants provide stability to the composition, as well as provide lathering, cleansing, mildness and other functions typically associated with surfactant. The surfactant needs to provide structure at full strength within a cleansing composition and then upon dilution the composition should rapidly transition to free surfactant micelles that lather, clean and deposit benefit agents. If the concentration of the structured surfactant is too high or increased to boost structure, these compositions generally have reduced mildness. If the compositions are over structured, then poor lathering results. Not having enough structurant can cause instability. Furthermore, achieving a balance between these two properties in the presence of larger, shaped abrasive particles can be difficult.

Therefore, there is a need for a new skin cleansing composition, e.g. body wash composition, comprising shaped biodegradable abrasive particles, having skin cleansing and/or exfoliating benefits when applied on skin surfaces and having a sufficiently acceptable surface safety profile on skin. It is also highly desirable that the skin cleansing composition is biodegradable, preferably in addition to the abrasive particles being biodegradable. The skin cleansing composition comprising shaped abrasive particles and lower levels of structuring surfactants herein also provide compositions having proper structure when at full strength and a micellar structure upon dilution. These compositions are also mild and the particles have adequate stability, visibility and tactile properties. Such a composition has not been recognized in the art.

SUMMARY OF THE INVENTION

In an embodiment a skin cleansing composition is provided comprising:
a. from about 0.1% to about 10% or from about 0.1% to about 1% by weight of the composition, of biodegradable abrasive particles comprising:
   i. a mean Circularity of from about 0.10 to about 0.60, or from about 0.15 to about 0.55, according to ISO 9276-6:2008;
   ii. a mean particle size as expressed by the area-equivalent diameter from about 500 µm to about 2000 µm, or from about 600 µm to about 1500 µm or from about 850 µm to about 1400 µm according to ISO 9276-6:2008;
   iii. a Biodegradable Rate of about 30% to about 100% or from about 40% to about 95%, as determined after 28 days according to the Biodegradability Test;
b. a surfactant phase selected from the group consisting of b(i) or b(ii);
   i. a structured surfactant phase comprising:
      1. from about 5% to about 20% or from about 5% to about 10% by weight of the composition, of a surfactant selected from the group consisting of STnS where n is between about 0 and about 3 or from about 0.5 to about 3 or from about 1.1 to about 3, isethionates, glycinates, succinates, glucosides, amphoacetates, ethanolamines, glutamates, taurates, betaines, phosphates, sarcosinates, sultaines, sulfonates, and combinations thereof;
      2. optionally from about 0% to about 10% of SLS;
      3. a structuring system comprising from about 0.05% to about 10% or from about 0.5% to about 5% by weight, of an electrolyte; and optionally from about 0.05% to about 0.5% of an associative polymer;
      wherein the composition has a Yield Stress of about 1 Pa to about 100 Pa;
   ii. a surfactant phase comprising:
      1. from about 5% to about 20% or from about 5% to about 14% by weight of the composition, of a surfactant selected from the group consisting of SLEnS where n is about 0 to about 3, isethionates, glycinates, succinates, glucosides, amphoacetates, ethanolamines, glutamates, taurates, betaines, phosphates, sarcosinates, sultaines, sulfonates, and combinations thereof;

2. optionally from about 0% to about 10% of SLS;
3. from about 0.05% to about 5% by weight, of an electrolyte, and
4. a structuring system comprising from about 0.05% to about 5% or about 0.05% to about 1% by weight of the composition, of a structuring material selected from the group consisting of an associative polymer, trihydroxystearin or combinations thereof;

wherein the composition has a Yield Stress of about 0.1 Pa to about 10 Pa.

The composition may also comprise a dermatologically acceptable carrier.

In another aspect, the present invention relates to a method for cleansing a human's skin surface comprising topically contacting the skin surface with a skin cleansing composition according to the present invention, and additionally followed by a rinsing step. It is an advantage of the compositions according to the present invention that they may be used to clean skin surfaces, while providing a good surface safety profile. A further advantage of the present invention is that in the compositions herein, the abrasive particles can be used at very low levels, while still providing the above benefits.

In another aspect, the present invention relates to use of biodegradable abrasive particles in a skin cleansing composition of the present invention, for delivering a benefit selected from the group consisting of mild skin exfoliation, dirt removal from a skin surface, and combinations thereof.

DETAILED DESCRIPTION OF THE INVENTION

Except as otherwise noted, the articles "a", "an", and "the" mean "one or more." The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain biodegradable abrasive particles, and one or more additional or optional ingredients as described hereinafter.

All percentages, parts and ratios are based upon the total weight of the compositions of the present invention, unless otherwise specified. All such weights as they pertain to listed ingredients are based on the active level and, therefore do not include carriers or by-products that may be included in commercially available materials. The components, including those which may optionally be added, as well as methods for preparation, and methods for use, are described in detail below.

All ratios are weight ratios unless specifically stated otherwise. All temperatures are in Celsius degrees (° C.), unless specifically stated otherwise.

As used herein "biodegradable" means chemical dissolution of the organic material by bacteria or other biological means at a certain rate (%) or above according to the Biodegradability Test as described in the Method Section herein.

As used herein "Biodegradable Test" means the test as described in the Method Section herein in which the test material is suspended in a phosphate buffered media containing an activated sludge inoculum and the formation of carbon dioxide measured via an electrolytic respirometer. The test material is the sole carbon and energy source and under aerobic conditions microorganisms metabolize organic substances producing $CO_2$ as the ultimate product.

As used herein "derivatives" means an ester, ether, amide, hydroxyl, and/or salt structural analogue of the relevant compound.

As used herein "dermatologically acceptable" means that the compositions or components described are suitable for use in contact with human skin tissue, preferably facial skin surfaces, without undue toxicity, incompatibility, instability, allergic response, discomfort, and the like.

As used herein "exfoliation" or "mild skin exfoliation" means removal of dead skin cells from the outermost layer of the skin whilst minimizing the risk of over-exfoliating the skin, which may otherwise result in damaged and/or redness to the skin, or discomfort to the user.

As used herein "surface safety profile" means that the compositions or components thereof are not overly abrasive to human skin tissue, particularly human facial skin tissue, so as to not scratch or damage the surface (e.g., redness) while still providing a good cleaning performance on the skin surface.

The term "anhydrous" as used herein, unless otherwise specified, refers to those compositions or materials containing less than about 10%, more preferably less than about 5%, even more preferably less than about 3%, even more preferably zero percent, by weight of water.

The term "multiphase" as used herein means that compositions comprise at least two phases which are chemically distinct (e.g. a surfactant phase and a benefit phase). Such phases are in direct physical contact with one another and are not separated by a barrier. In one aspect of the invention, the composition can be a multiphase composition where the phases of the composition are blended or mixed to a significant degree. In another aspect of the invention, the composition can be a multiphase composition where the phases of the composition are made to occupy separate but distinct physical spaces inside the package in which they are stored, but are in direct contact with one another (i.e., they are not separated by a barrier and they are not emulsified or mixed to any significant degree).

The term "skin cleansing composition" as used herein, refers to compositions intended for topical application to the skin or hair. The compositions of the present invention are rinse-off formulations, in which the product is applied topically to the skin or hair and then is subsequently rinsed within minutes from the skin or hair with water, or otherwise wiped off using a substrate with deposition of a portion of the composition. The compositions also may be used as shaving aids. The composition of the present invention is typically extrudable or dispensible from a package.

The compositions of the present invention can be in the form of liquid, semi-liquid, cream, lotion or gel compositions intended for topical application to skin. Examples of skin cleansing compositions of the present invention can include but are not limited to shampoo, conditioning shampoo, body wash, moisturizing body wash, shower gels, skin cleansers, cleansing milks, hair and body wash, in shower body moisturizer, pet shampoo, shaving preparations and cleansing compositions used in conjunction with a disposable cleansing cloth and bar soap.

The phrase "substantially free of" as used herein, unless otherwise specified means that the composition comprises less than about 5%, preferably less than about 3%, more preferably less than about 1% and most preferably less than about 0.1% of the stated ingredient. The term "free of" as used herein means that the composition comprise 0% of the stated ingredient that is the ingredient has not been added to the composition, however, these ingredients may incidentally form as a byproduct or a reaction product of the other components of the composition.

The term "surfactant component" as used herein means the total of all anionic, nonionic, amphoteric, zwitterionic and cationic surfactants in a phase. When calculations are based on the surfactant component, water and electrolyte are excluded from the calculations involving the surfactant component, since surfactants as manufactured typically are diluted and neutralized.

The term "STnS" as used herein, means sodium trideceth sulfate, where n is defined as the average number of moles of ethoxylate per molecule. Trideceth is a 13 carbon branched ethoxylated hydrocarbon comprising, in one embodiment, an average of at least 1 methyl branch per molecule.

The term "SLS" as used herein, means sodium lauryl sulfate.

The term "SLEnS" as used herein, means sodium laureth sulfate, where n is defined as the average number of moles of ethoxylate per molecule.

The term "lather" as used herein, means the aerated foam which results from providing energy to aqueous surfactant mixtures, especially dilute mixtures. Lather is increased in micellar compositions compared to structured, e.g., lamellar compositions, so that a phase change during dilution to micelles typically increases lather.

Biodegradable Abrasive Particles

The skin cleansing compositions herein comprises biodegradable abrasive particles that are selected or synthesized to possess the desired shapes, as defined by certain parameters, such as for non-limiting example: Circularity, Solidity, and/or adequate hardness, to be effective for cleansing skin surfaces. In an embodiment, the biodegradable abrasive particles have an acceptable surface safety profile and thus are not overly abrasive on contact with skin. In another embodiment, the biodegradable abrasive particles are dermatologically acceptable.

The term "biodegradable" in reference to the abrasive particles, means that the abrasive particles of the present invention have a Biodegradability Rate of at least about 30%, preferably at least about 35%, or more preferably at least about 40%, as determined after 28 days according to the Biodegradability Test as disclosed herein. In a preferred embodiment, the Biodegradable Rate of the abrasive particles is at most about 100%, 99%, 95%, 90%, 85% or 80%.

The biodegradable abrasive particles are selected from the group of polymeric material consisting of:
  (a) one or more homo-polymers or co-polymers selected from the group consisting of polyhydroxy alkanoate (PHA), polylactic acid derivatives (PLA), polycaprolactone (PLC), poly(glycolic acid) (PGA), and blends thereof;
  (b) aliphatic and/or, aromatic co-polyesters, preferably wherein the co-polyester is selected from co-polyester containing succinic, glutaric, adipic, terephtalic diacids, propanediol, butanediol, pentanediol, hexanediol monomer or blends thereof, preferably polybutylene succinate (PBS), or polybutylene-adipate-terephtalate (PBAT);
  (c) starch, thermoplastic starch (TPS), or blends thereof;
  (d) thermoplastic cellulose (TPC) derivative selected from the group consisting of cellulose ester, cellulose ether, cellulose alkanoate and blends thereof, preferably the thermoplastic cellulose is cellulose acetate, nitrocellulose or blends thereof; and
  (e) combinations of (a) to (d).

In a preferred embodiment, the polymeric material is polyhydroxy alkanoate (PHA) selected from the group consisting of poly-3-hydroxybutyrate (PHB), poly-3-hydroxyhexanoate, poly-3-hydroxy-valerate, poly-3-hydroxy-butyrate-co-3-hydroxyvalerate (PHBV), poly-3-hydroxybutyrate-co-3-hydroxyhexanoate, and blends thereof.

In a preferred embodiment, the biodegradable abrasive particle of the present invention are poly-3-hydroxybutyrate-co-3-hydroxyvalerate (PHBV). PHBVs are biopolymers that are synthesized by bacteria as intracellular carbon and energy storage granules under limited nutrients in the presence of excess carbon source. The molecular weight of these polymer varies from 200,000 g/mol to 3,000,000 g/mol depending on the microorganism, nutrients and growth conditions. The molecular weight of PHBV polymers ranges from 1,000 g/mol to 3,000,000 g/mol, preferably from 20,000 g/mol to 700,000 g/mol, more preferably from 100,000 g/mol to 500,000 g/mol.

In certain embodiments, the biodegradable abrasive particles of the present invention are reduced into particles from polymeric foam material, by grinding or milling Biodegradable abrasive particles may also contain minor components of process aids well known in the art, such as crystal nucleating agents, anti-oxidants, stabilizers, and rheology modifiers. In an embodiment the biodegradable polymer is blended with abundant amount of mineral or vegetable and soluble or insoluble filler. Inclusion of a large quantity of filler helps break the polymer into abrasive particles and features biodegradable particles with large surface areas (e.g., via porosity and capillarity) which enhance the degradation kinetics. This is especially the case when the filler is water soluble. Typical fillers suitable for use with PHBV polymers are minerals (e.g., metal chlorides such as for example, NaCl, KCl, etc.; metal carbonates such as for example, $Na_2CO_3$, $NaHCO_3$, etc.; metal sulfates such as for example, $MgSO_4$), generally all mineral adsorbents provide hardness, which is compatible with the overall target hardness of the biodegradable abrasive cleaning particle.

The filler can also be derived from vegetal feedstock, essentially from cellulose or lignocelluloses based material (e.g., nut shell, wood or bamboo fibers, corn cob, rice hull, etc. including carbohydrates such starch and flour, xanthan gum, alginic, dextran, agar, and the like). The suitable fillers are also biodegradable and do not change the biodegradability of the final abrasive particles or biodegradability of the skin cleansing composition.

Typical biodegradable PHBV polymers comprise filler from about 10 wt % to 70 wt %, preferably from 20 wt % to 60 wt %, or most preferably from 40 wt % to 50 wt %, wherein wt % is relative to the total weight of the PHBV polymer materials.

The applicant has surprisingly found that biodegradable abrasive particles according to the present invention, when formulated into the skin cleansing compositions, provide good cleaning/cleansing performance on human skin surfaces, while providing a good surface safety profile. In particular, by controlling the shapes of the biodegradable abrasive particle, through selection or synthesis, to be non-rolling and not overly sharp, a benefit is delivered and is selected from the group consisting of mild skin exfoliation, good dirt removal from a skin surface, and combinations thereof, preferably without damaging the skin surface or causing discomfort to the users to provide a acceptable surface safety profile. By "non-rolling", it is meant that the abrasive particles slide across the skin surface rather than roll across the surface. It is believed that this non-rolling character promotes improved cleansing efficacy and exfoliation benefits.

The shapes of the biodegradable abrasive particles can be defined in various ways. The present invention defines effective shapes, for example, by mean Circularity and mean Solidity. The present invention defines the shapes of the biodegradable abrasive particle in the form of particles, which reflects the geometrical proportions of a particle and more pragmatically of the particle's population. Analytical techniques allow an accurate simultaneous measurement of particle shapes from a large number of particles, typically greater than 1,000, preferably greater than 10,000 particles (more preferably above 100,000 particles). This enables accurate tuning and/or selection of average particle population shape with discriminative performance. These measurement analyses of particle shape are conducted using on Occhio Nano 500 Particle Characterization Instrument with its accompanying software Callistro version 25 (Occhio s.a. Liege, Belgium) or the latest version available. This instrument is used to prepare, disperse; image and analyze the particle samples, as per manufacturer's instructions, and the following instrument setting selections: White Requested=180, vacuum time=5,000 ms, sedimentation time=5,000 ms, automatic threshold, number of particles counted/analyses=8,000 to 500,000, minimum number of replicates/sample=3, lens setting 1×/1.5×.

Circularity

The term "Circularity" means a quantitative, 2-dimensional image analysis shape description and is being measured according to ISO 9276-6:2008(E) section 8.2 as implemented via the Occhio Nano 500 Particle Characterization Instrument with its accompanying software Callistro version 25 (Occhio s.a. Liege, Belgium) or the latest version available. Circularity is a preferred mesoshape descriptor and is widely available in shape analysis instrument such as in Occhio Nano 500 or in Malvern Morphologi G3. Circularity is sometimes described in literature as being the difference between a particle's shape and a perfect sphere. Circularity values range from 0 to 1, where a circularity of 1 describes a perfectly spherical particle or disc particle as measured in a two dimensional image.

$$C = \sqrt{\frac{4\pi A}{P^2}}$$

Where A is projection area, which is 2D descriptor and P is the length of the perimeter of the particle.

By the term "mean Circularity" the applicant considers the average of the circularity values of each particle taken from a population of at least 1,000, preferably above 10,000 particles, preferably above 50,000 particles, more preferably above 100,000 particles, after excluding from the measurement and calculation, the circularity of particles having area-equivalent diameter (ECD) of below 10 micrometers. Mean data are extracted from volume-based vs. number-based measurements.

The applicant has found that the biodegradable abrasive particles having a mean Circularity to meet the surface safety criteria and promote effective skin cleansing from about 0.10, 0.15, 0.20 to about 0.45, 0.55, or 0.60. In certain embodiment, the abrasive particles have a mean Circularity of about 0.20 to about 0.45, as determined according to ISO 9276-6:2008(E) section 8.2.

Solidity

The term "Solidity" means a quantitative, 2-dimensional image analysis shape description, and is being measured according to ISO 9276-6:2008(E) section 8.2 as implemented via the Occhio Nano 500 Particle Characterization Instrument with its accompanying software Callistro version 25 (Occhio s.a. Liege, Belgium). In an embodiment the non-spherical particle herein has preferably at least one edge or surface having a concave curvature. Solidity is a mesoshape parameter, which describes the overall concavity of a particle/particle population. Solidity values range from 0 to 1, where a solidity number of 1 describes a non-concave particle, as measured in literature as being:

Solidity=$A/Ac$

Where A is the area of the particle and Ac is the area of the convex hull (envelope) of bounding the particle.

By the term "mean Solidity" the applicant considers the average of the solidity or roughness values of each particle taken from a population of at least 1,000 preferably above 10,000 particles, preferably above 50,000 particles, more preferably above 100,000 particles, after excluding from the measurement and calculation, the solidity or roughness data of particles having area-equivalent diameter (ECD) of below 10 micrometers. Mean data are extracted from volume-based vs. number-based measurements.

The applicant has found out that biodegradable abrasive particles having a defined mean Solidity from about 0.60, 0.65, 0.70, or 0.75, 0.80 to about 0.90, 0.95, or 1.0. In certain embodiment, the biodegradable abrasive particles have a mean Solidity from about 0.80 to about 1.0, as determined according to ISO 9276-6:2008(E) section 8.2. Alternatively, the biodegradable abrasive particles have a mean Solidity of between from about 0.60 to about 1.0 or preferably from about 0.80 to about 1.0, as determined according to ISO 9276-6:2008(E) section 8.2.

The term "Solidity" is sometimes also named "Convexity" in literature or in some apparatus software using the solidity formula in place of its definition described in ISO 9276-6 (convexity=Pc/P where P is the length of the perimeter of the particle and Pc is length of the perimeter of the convex hull—envelope—bounding the particle). Despite solidity and convexity being similar mesoshape descriptor in concept, the applicants refer herein to the solidity measure expressed above by the Occhio Nano 500, as indicated above.

Hardness

The biodegradable abrasive particles should be hard enough to provide good cleaning/cleansing performance while providing good surface safety and/or skin feel acceptability. The biodegradable abrasive particles in the present invention may have Shore® D hardness from about 35, 40, 45, or 50 durometer to about 60, 65, or 75 durometer as determined according to ASTM D2240-05 (2010). Shore® D hardness measurement is carried out by using an ASTM durometer, such as the Type D Style Durometer available from Pacific Transducer Corp. of Los Angeles, Calif., or from ELECTROMATIC Equipment Co., Inc. 600 Oakland Ave Cedarhurst, N.Y. 11516 (description of the stylus digital or gauge instrument at http://www.checkline.com/durometers)

Mean Particle Size

The applicant has found that good skin cleansing efficiency can be achieved with the biodegradable abrasive particles having a certain mean particle size as defined by their area-equivalent diameter (ISO 9276:2008(E) section 7) also called Equivalent Circle Diameter (ECD) (ASTM F1877-05 Section 11.3.2). Mean ECD of particle population is calculated as the average of respective ECD of each particle of a particle population of at least 1,000 preferably above 10,000 particles, preferably above 50,000 particles, more preferably above 100,000 particles after excluding from the measurement and calculation the data of particles having area-equivalent diameter (ECD) of below 10 micrometers. Mean data are extracted from volume-based vs. number-based measurements. In an embodiment, biodegradable abrasive particles have a mean particle size as expressed by the area-equivalent diameter of from about 500 μm, 650 μm, or 850 μm to about 1,000 μm, 1,200 μm, 1,500 μm, 2,000 μm or preferably from about 850 μm to about 1,400 μm.

Figure 1:
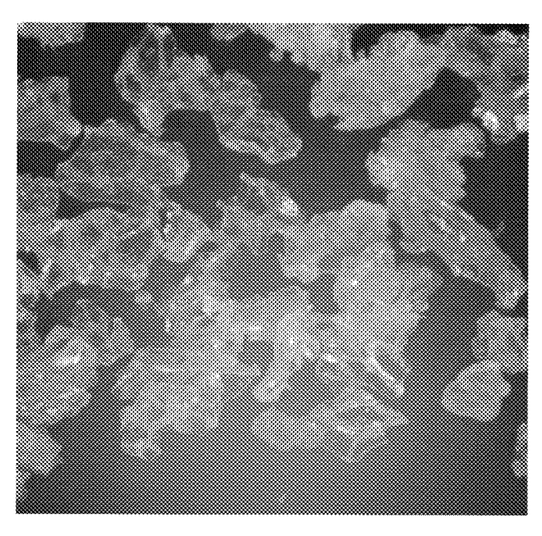
FIG. 1 is a microscopy image showing ground PHBV biodegradable abrasive particles having a circularity of about 0.3 to about 0.5, an ECD particle size from 850 μm to 1400 μm and a solidity of about 0.7 to about 0.8.

FIG. 1 is a microscopy image showing ground PHBV biodegradable abrasive particles having a circularity of about 0.3 to about 0.5, an ECD particle size from 850 μm to 1,400 μm and a solidity of about 0.7 to about 0.8.

Typical shearing or graining methods may be used to reduce the above material into biodegradable abrasive particles featuring useful shapes. Thereafter, grain shaping methods described in the art may be employed such as agglomerating, printing, carving, etc. As examples, suitable ways of reducing the biodegradable abrasive material into abrasive cleaning particles herein is to grind or mill the material using jaw Crushers mills or rotor mills or cutting or blade or knife mills, or impact or rotor or disc mills such as manufactured by Retschz (see http://www.retsch.com/products/milling). If needed the temperature needs to be kept constant during the grinding operation, whereas suitable grinding temperature should not exceed 60° C. In most cases, the optimal grinding temperature needs to be below 30° C., sometimes below 0° C. and in cases grinding is better achieved in cryogenic condition using refrigerant media such as $CO_2$ or nitrogen in liquid conditions.

Other suitable means include the use of eroding tools such as a high speed eroding wheel with dust collector wherein the surface of the wheel is engraved with a pattern or is coated with abrasive sandpaper or the like to promote formation of the abrasive cleaning particles herein.

Alternatively the abrasive raw material can be broken into pieces of a few centimeter dimensions by manually chopping or cutting, or using a mechanical tool such as a lumpbreaker, for example the Model 2036 from S Howes, Inc. of Silver Creek, N.Y.

Preferably, the abrasive cleaning particles obtained via grinding or milling operation are single particles.

Shaping processes are sometimes facilitated by mixing previous biodegradable abrasive materials as fillers within a thermoplastic or solidifying matrix. Such processes e.g.: including selection of matrix and respective load of filler are well known in art. One way to accurately achieve the desired shape of the particle, is to foam the biodegradable abrasive raw material per se or biodegradable abrasive material dispersed within a matrix and reducing the foam into biodegradable abrasive particles with improved efficiency. Foaming processes and foam structure are typically achieved via gas expansion process, e.g.: either by injecting gas or solvent within the biodegradable abrasive precursor material and allowing expansion by pressure drop and/or increasing of temperature e.g.: extrusion foaming process or more conveniently with in-situ generated gas followed by hardening of the biodegradable abrasive precursor material e.g.: polyurethane foaming process. Alternatively, foam structures can also be achieved via emulsion process, followed by hardening and drying step.

In an embodiment herein, to achieve the geometrical shape descriptors of the biodegradable abrasive cleaning particles (i.e. circularity, solidity) the biodegradable abrasive cleaning particles are obtained from foamed polymeric material, which is reduced into the biodegradable abrasive particles preferably by grinding or milling as described herein.

In one embodiment the abrasive particles are made from a process comprising:
a. Foaming the abrasive particle material wherein the foam has a density from $100 \text{ kg/m}^3$ to $500 \text{ kg/m}^3$, more preferably from $100 \text{ kg/m}^3$ to $500 \text{ kg/m}^3$ or from $5 \text{ kg/m}^3$ to $100 \text{ kg/m}^3$ or from $25 \text{ kg/m}^3$ to $50 \text{ kg/m}^3$ wherein the foam has an open or close-cell structure;
b. Adjusting the foam cell size from 20 micrometers to 2000 micrometers or from 100 to 1000 micrometers or from 200 to 500 micrometers wherein foam cell size can be measured for instance using protocol described in ASTM D3576;
c. Determining the target particle size and maintaining the cell size so that it is at least two times the size of the target or the target size to be is no less than about half of the foam cell size.
d. Preferably the biodegradable abrasive cleaning particles obtained via grinding or milling operation are single particles, which have little remaining cell structure.

Further, in another embodiment when large particle size is desired, foam with larger cell size is desirable and vice-et-versa.

Additionally, in order to favor the reduction of the foam into particles, the foam may have little tendency to deform and is liable to fracture. This behavior may result if the polymer has a glass transition temperature significantly higher than the usage temperature or if the polymer has a high degree of crystallinity and the crystalline melting temperature is significantly above the usage temperature.

Alternatively and in a highly preferred embodiment herein, the foam may be reduced to particles in several stages. First the bulk foam can be broken into pieces of a few centimeter dimensions by manually chopping or cutting, or using a mechanical tool such as a lumpbreaker, for example the Model 2036 from S Howes, Inc. of Silver Creek, N.Y.

The applicant has found that gentle cleaning will be achieved with the biodegradable abrasive particles, which have been made from a foam having density above $200 \text{ Kg/m}^3$, preferably above $400 \text{ Kg/m}^3$ and even more preferably above $600 \text{ Kg/m}^3$ since the particle after grinding will have shape with lower angularity, and significantly better skin cleaning effect can be achieved with the foam density being below $200 \text{ Kg/m}^3$, more preferably from $25 \text{ Kg/m}^3$ to $50 \text{ Kg/m}^3$ since the particle after grinding will have shape with higher angularity. In an embodiment particles are made from grinding polymeric foam with density ranging $100 \text{ Kg/m}^3$ to $400 \text{ Kg/m}^3$.

Skin Cleansing Compositions

The present invention is directed to a skin cleansing composition comprising: biodegradable abrasive particles present at a level of from about 0.1 wt % to about 10 wt %, preferably from about 0.1 wt % to about 1 wt %, more preferably from about 0.2 wt % to about 1 wt %, and a dermatologically acceptable carrier.

The skin cleansing compositions according to the present invention are designed as skin cleansers for a variety of human skin surfaces. Examples of the skin cleansing compositions include, a facial cleanser, a body wash, a hand cleanser, a bar soap, or a body cleanser. In a preferred embodiment, the skin cleansing compositions herein are suitable for use as a body wash.

In a preferred embodiment, the skin cleansing compositions according to the present invention are considered "biodegradable" as determined by the Biodegradability Test as disclosed in the Method Section herein. Biodegradation is the chemical dissolution of materials by bacteria or other biological means. Currently, biodegradability is commonly associated with environmentally friendly products that are capable of decomposing back into natural elements. Organic material can be degraded aerobically with oxygen, or anaerobically without oxygen. Readily biodegradable materials discussed herein are materials which biodegrade according to protocol and requirement described in Biodegradability Test as disclosed in the Method Section here. This Biodegradability Rate would include all components except for inorganic materials and water.

In one embodiment, the term "biodegradable" in reference to the skin cleansing compositions means a skin cleansing composition having a Biodegradability Rate of about 30% to about 100% or at least about 60%, preferably at least about 70%, more preferably at least about 80%, or even more preferably at least 90%, as determined after 28 days according to the Biodegradability Test as disclosed herein. In another embodiment herein, the Biodegradable Rate of the skin cleansing composition is at most about 100%, 99%, 95%, 90%, 85% or 80%.

In another embodiment, the skin cleansing compositions have a viscosity in the range of from about 100 cps to about 1,000,000 cps, preferably from about 1,000 to about 300,000 cps, or more preferably from about 5,000 to about 200,000 cps. The viscosity are measured at 20 sec$^{-1}$ and 20° C. with a Rheometer, model AR 1000 (Supplied by TA Instruments) with a 4 cm conic spindle in stainless steel, 2° angle (linear increment from 0.1 to 100 sec$^{-1}$ in max. 8 minutes).

In another embodiment, the skin cleansing compositions herein are neutral compositions. In other preferred embodiments, the skin cleansing compositions herein have a pH in the range of from about 5.0 to about 8.0, more preferably from about 5.5 to about 7.5, more preferably from about 5.5 to about 6.5, wherein the pH is measured at 25° C.

Accordingly, the skin cleansing compositions herein may comprise suitable bases and acids to adjust the pH. A suitable base to be used herein is an organic and/or inorganic base. Suitable bases for use herein are the caustic alkalis, such as sodium hydroxide, potassium hydroxide and/or lithium hydroxide, and/or the alkali metal oxides such as, sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (e.g., monoethanolamine), urea and urea derivatives, polyamine, etc. Typical levels of such bases, when present, are from about 0.01 wt % to about 5.0 wt %, preferably from about 0.05 wt % to about 3.0 wt %, and more preferably from about 0.1 wt % to about 0.6 wt %, wherein the wt % is relative to the total weight of the composition.

The skin cleansing compositions herein may comprise an acid to trim its pH to the required level, despite the presence of an acid, if any, the skin cleansing compositions herein will maintain their preferred neutral, pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of the acids may be commercially available from BASF under the trade name Sokalan® DCS. A suitable inorganic acid is selected from the group consisting of hydrochloric acid, sulfuric acid, phosphoric acid and a mixture thereof. A typical level of such an acid, when present, is from about 0.01 wt % to about 5.0 wt %, preferably from about 0.04 wt % to about 3.0 wt % and more preferably from about 0.05 wt % to about 1.5 wt %, wherein the wt % is relative to the total weight of the composition.

The term "structured" or "structuring" as used herein means having a rheology that confers stability on the composition. The degree of structure is determined by characteristics determined by the Yield Stress Method, in the Test Methods below. Accordingly, a surfactant phase of the composition of the present invention is considered "structured," if the surfactant phase has one or more of the following properties: a Yield Stress of about 1 Pa to about 100 Pa (Pascal) for b(i) and Yield Stress of about 0.1 Pa to about 10 Pa for b(ii).

Cleansing/Surfactant Phase

One of the phases of the skin cleansing composition of the present invention is a cleansing phase, which is a surfactant phase. The surfactant phase may comprise a structured domain that comprises a surfactant and optionally a cosurfactant. The structured domain may be an opaque structured domain, which is preferably a lamellar phase. The lamellar phase can provide resistance to shear, adequate yield strength to suspend particles and droplets and at the same time provides long term stability, since it is thermodynamically stable. The lamellar phase tends to have a viscosity that minimizes the need for viscosity modifiers.

Examples of some suitable branched surfactants include anionic surfactants such as the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and combinations thereof. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al. on Jan. 1, 2002. Suitable examples of alcohols are Safol™ 23 and Neodol™ 23. Suitable examples of alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

The surfactant may also be STnS, wherein n can define average moles of ethoxylation. A structured cleansing phase can include from about 5% to about 20%, from about 7% to about 18%, from about 5% to about 10%, from about 9% to about 16%, from about 11% to about 14%, by weight of the composition, of STnS, wherein n can range from about 0 to about 3, from about 0.5 to about 3, from about 1.1 to about 3. Such described benefits of STnS are disclosed in U.S. patent application Ser. No. 13/157,665.

A material such as ST2S or ST3S, for example, may comprise a significant amount of molecules which have no ethoxylate, 1 mole ethoxylate, 2 mole ethoxylate, and so on in a distribution which can be broad, narrow or truncated, still comprising ST2S wherein the average of the distribution is about 2 or ST3S wherein the average of the distribution is about 3.

STnS is optionally combined with SLS in order to form a surfactant system. In one embodiment, the skin cleansing compositions of the present invention comprise less than about 5% SLS, alternatively less than about 4% SLS, alternatively less than about 3% SLS, alternatively less than about 2% SLS, alternatively less than about 1% SLS, alternatively between about 0.1% SLS and about 2% SLS, alternatively about 0% SLS. Without wishing to be bound by theory, it is believed that the presence of SLS increases the harshness of the composition, negating at least in part the mildness benefits and/or the efficacy of the benefit agents within the skin cleansing composition.

Further, the surfactant phase can comprise a structuring system wherein the structuring system can comprise an associative polymer, a non-associative polymer, an electrolyte, trihydroxystearin, and combinations thereof. The structuring system can comprise from about 0.05% to about 5%, from about 0.05% to about 1%, from about 0.07% to about 0.5%, or from about 0.1% to about 0.3%, by weight of the composition, of a structuring material such as a non-associative polymer. The structuring system can comprise from about 0.001% to about 5%, from about 0.005% to about 0.5%, from about 0.007% to about 0.05%, from about 0.008% to about 0.04%, or from about 0.01% to about 0.03%, by weight of composition, of an associative polymer. As noted herein, stability of a composition can be maintained or enhanced even with the reduction of associative polymer with the addition of a non-associative polymer. In an embodiment the composition may comprise from about 0.05% to about 5%, from about 0.05% to about 1% by weight of the composition, of a structuring material selected from the group consisting of an associative polymer, trihydroxystearin or combinations thereof.

Associative polymers can be crosslinked, alkali swellable, associative polymers comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in the presence of an electrolyte. The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis or by analytical techniques such as proton nuclear magnetic resonance (NMR). Associative alkyl side chains can comprise, for example, butyl, propyl, stearyl, steareth, cetyl, lauryl, laureth, octyl, behenyl, beneath, or other linear, branched, saturated, or unsaturated alkyl or alketh hydrocarbon side chains.

Crosslinked, associative polymers having certain % HM and certain carbon numbers of hydrophobic end groups of alkyl side chains can provide significant enhancement of structure to compositions comprising a structured surfactant, especially to compositions comprising reduced levels of surfactant. Such associative polymers can also provide the above structure at surprisingly low levels of polymer structurant. Concentrations of associative polymers of up to about 5% or even 10% have been known to provide a sufficient amount of structure (e.g., exemplary compositions of U.S. Pat. No. 7,119,059 (Librizzi, et al.) and U.S. Pat. No. 6,897,253 (Schmucker-Castner, et al.). When an associative polymer % HM and an alkyl side chain number of carbons can be optimized, the structure of an aqueous structured surfactant phase can be increased using only less than about 3 wt %, less than about 2%, less than about 1%, and less than about 0.2%, of an associative polymer, as a percentage of an aqueous structured surfactant phase.

The acidic monomer can comprise any acid functional group, for example sulfate, sulfonate, carboxylate, phosphonate, or phosphate or mixtures of acid groups. The acidic monomer can comprise, for example, a carboxylate. Alternatively, the acidic monomer can be an acrylate, including acrylic acid and/or methacrylic acid. The acidic monomer can comprise a polymerizable structure, e.g., vinyl functionality. Mixtures of acidic monomers, for example acrylic acid and methacrylic acid monomer mixtures, may be useful as well.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth)acrylate is understood to mean either methyl acrylate or acrylate, or mixtures of the two.

Sometimes, the hydrophobic end group of the associative polymer can be incompatible with the aqueous phase of the composition and can associate with lathering surfactant hydrophobe components. Without intending to be limited by theory, it is believed that longer alkyl chains of structuring polymer hydrophobe end groups can increase incompatibility with the aqueous phase to enhance structure, whereas shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the composition comprising a structured surfactant with low levels of polymer structurant.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% HM. Associative polymers can comprise about $C_{16}$ (cetyl) alkyl hydrophobic side chains with about 0.7% hydrophobic modification, but a percentage hydrophobic modification can be up to an aqueous solubility limit in surfactant compositions (e.g., up to 2%, 5%, or 10%). Other associative polymers can include stearyl, octyl, decyl and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

As set forth above, the structured cleansing phase of a composition can further include a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), and synthetic hydrocarbon polymers (e.g., polyacrylamide and copolymers, polyethylene oxide, polyacrylic acid copolymers).

As set forth above, the structured surfactant phase or surfactant phase may comprise from about 0.05% to about 10% or from about 0.5% to about 5% by weight, of an electrolyte. The electrolyte may comprise an anion selected from the group consisting of phosphate, chloride, sulfate, citrate, and mixtures thereof, and a cation selected from the group consisting of sodium, ammonium, potassium, magnesium, and mixtures thereof. The electrolyte may also be selected from the group consisting of sodium chloride, ammonium chloride, sodium sulfate, ammonium sulfate, and mixtures thereof.

The composition can be optionally free of or substantially free of sodium lauryl sulfate, hereinafter SLS, and/or ammonium lauryl sulfate, hereinafter ALS, and can comprise at least a 70% lamellar structure. However, in an alternative arrangement, the structured cleansing phase can comprise at least one surfactant, wherein the at least one surfactant includes SLS and/or ALS. Suitable examples of SLS are described in U.S. patent application Ser. No. 12/817,786.

Cosurfactant

The skin cleansing compositions of the present invention may further comprise a cosurfactant. Cosurfactants in the present invention comprise from about 0.1% to 20%, alternatively from about 1% to about 10% by weight of the composition. Cosurfactants of the present invention comprise amphoteric surfactants, zwitterionic surfactants, and mixtures thereof. In one embodiment, the composition comprises at least one amphoteric surfactant and/or at least one zwitterionic surfactant. Amphoteric surfactants suitable for use in the present invention include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. In one aspect, the multiphase composition can comprise an amphoteric surfactant that is selected from the group consisting of sodium lauroamphoacetate, sodium cocoamphoacetate, disodium lauroamphoacetate, disodium cocodiamphoacetate, and mixtures thereof. Moreover, amphoacetates and diamphoacetates can also be used.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase composition include betaines, including cocoamidopropyl betaine.

Carrier

The skin cleansing composition may comprise a dermatologically acceptable carrier.

Dermatologically acceptable carriers may be selected for various stability, aesthetics, and/or compatibility with other materials present in the skin cleansing composition. Suitable carriers include water and/or water soluble solvents. The skin cleansing composition may comprise from about 1% to about 95% by weight of water and/or water equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, octanediol, ethylhexanediol, decanediol; glycerin; water, and mixtures thereof. In certain embodiments, the skin cleansing composition comprises water, diols, glycerin, and combinations thereof.

Suitable carriers also include oils. The skin cleansing composition may comprise from about 1% to about 95% by weight of one or more oils. Oils may be used to solubilize, disperse, or carry materials that are not suitable for water or water-equivalent solvents. Suitable oils include silicones, hydrocarbons, esters, fatty amides, ethers, and mixtures thereof. Oils may be fluid at room temperature. However, certain skin cleansing product forms (i.e., solid or semisolid stick) may require non-fluid oils. The oils may be volatile or nonvolatile. "Non-volatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm Hg at 25° C. Volatile oils may be used to provide a lighter feel when a heavy, greasy film is undesirable.

Suitable oils include volatile oils. In certain embodiments, the volatile oils may have a viscosity ranging from about 0.5 to about 5 centistokes (cst) at 25° C. Volatile oils may be used to promote more rapid drying of the skin care composition after it is applied to skin.

Non-volatile oils are also suitable for use in the composition. Non-volatile oils are often used for emolliency and protective properties. Non-volatile oils preferably may have a viscosity ranging from about 5 cst to about 2,000,000 cst or from about 20 cst to about 200,000 cst. Suitable examples of oils for use in the skin cleansing composition of the present invention are found in U.S. 2013/039961 (P&G).

Optional Skin Cleansing Ingredients

The skin cleansing composition may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, phytosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratine protecting agents, emollients, moisturizers, and combinations thereof.

Method of Using the Skin Cleansing Compositions

The present invention encompasses a method for cleansing a human's skin surface comprising topically contacting the skin surface with a skin cleansing composition according to the present invention. Suitable skin surfaces herein include body, hands, and facial skin surfaces.

In a preferred embodiment, the composition according to the present invention is topically applied to the body or facial skin surface. "Facial skin surface" refers to one or more of the forehead, periorbital, cheek, perioral, chin, and nose skin surfaces.

The composition herein may be in its neat form or in its diluted form. By "in its neat form", it is to be understood that the composition is applied directly onto the skin surface to be treated without undergoing any dilution. By "diluted form", it is meant herein that the composition is diluted by the user typically with water. The composition is diluted prior to use to a typical dilution level of up to 10 times its weight of water. As usually recommended dilution level is a 10% dilution of the composition in water.

The composition herein may be applied using the palms of the hands and/or fingers, or using an appropriate implement, such as a puff, loofah, cloth, sponge, mask, razor, wand, cotton ball, swab, or pad, soaked in the diluted or neat composition herein. Furthermore, once applied onto the skin surface the composition may be agitated over the skin surface.

The method herein may optionally contain an additional rinsing step, preferably after the application of the composition. By "rinsing", it is meant herein contacting the surface cleaned/cleansed with the method according to the present invention with substantial quantities of appropriate solvent, typically water, directly after the step of applying the liquid composition herein onto the skin surface. By "substantial quantities", it is meant herein between 0.001 L and 1 L of water per $m^2$ of skin surface, more preferably between 0.1 L and 1 L of water per $m^2$ of skin surface.

Test Methods i.) Cleansing Efficacy

Validation products used are a market Old Spice Pure Sport Bar Soap, a market Old Spice Pure Sport Body Wash.

This method has the following reliability parameters: Within the same set of conditions, a single operator can get repeatable results within the ranges as per product type. Likewise, comparison of average results across different operators indicates reproducibility of results within the given ranges.

The method has relative standard deviations within the 20% range. The pressure used during cleaning has large impact on data reliability. About a one Newton force is used. Every sample is measured 3 times. Results are calculated as the Delta E difference between untreated and treated stains. Delta E results should be rounded to the nearest whole number.

1. PROCEDURE
    1.1. Equipment/Materials needed:
        1.1.1. Sink and counter top; faucet has running city water and is controlled for temperature and flow rate.
        1.1.2. Black Todd Clay stains on 100% polyester fabrics (Polycon100) supplied by APD (Accurate Product Development, Fairfield, Ohio, 45014). Stains and/or fabric may be modified upon re-validation.
        1.1.3. Substrate pad (if performing the body wash with substrate protocol) made by heat-sealing a textured polyethylene substrate material around a 3"×4" piece of plastic shelf liner:
            textured purple substrate, supplied by Tredegar, # X-37559.
            white plastic shelf liner, made by Easy Liner, Solid Grip.
        1.1.4. White Bounty paper towels.
        1.1.5. Powder-free Nitrille disposable gloves.
        1.1.6. Scissors.
        1.1.7. Sharpie marker.
        1.1.8. Timer.
        1.1.9. 1 ml plastic disposable syringes.
        1.1.10. Chromameter with hand-held single sample L,a,b measurement capability. (Minolta Chromameter CR-300)
        1.1.11. White Easy Liner Solid Grip shelf liner, at least 3"×4" piece or larger, as background surface for stained fabric color readings.
    1.2. Overview:
        1.2.1. The overall procedure involves the cleaning by hand of specified stains from specified fabric surfaces. The cleaned stains are allowed to dry, and L,a,b color measurements are taken of the stains using a Minolta Chromameter. The calculated difference between untreated and treated stains provides the Delta E measurement of cleaning. Three replicates are measured per sample. Two controls must also be tested, a low control of an Old Spice Bar Soap and a high control of an Old Spice Body Wash and meet specified Delta E ranges. Calculate L,a,b data to Delta E results vs. untreated stains, where:

Delta $E$=Square Root of (Delta $L$ squared+Delta $a$ squared+Delta $b$ squared).

1.2.2. At least 3 replicates (hand clean 3 stained fabrics) per sample, one at a time.
        1.2.3. Wear clean gloves (powder-free Nitrile).

1.2.4. Turn on running tap water at a sink and adjust temperature to 38° C., with flow rate=1.4-1.6 gpm.

1.2.5. Hold the stained fabric (stain side up) under faucet with both hands & moisten the stain for 1 second with a single back and forth motion under running tap water. Place on dry counter top surface (stain side up).

1.3. For Bar Soap:

1.3.1. Hold bar under the running tap water and rotate bar 3 complete revolutions (=6 half rotations) in both hands with moderate pressure.

1.3.2. Using the bar, scrub the stain for 5 seconds—using 10 circular motions and moderate pressure, at a rate of 2 circular motions per second.

1.4. For Body Wash:

1.4.1. Wet the hand that will clean the stain for 1 second under running tap water.

1.4.2. Using the other hand, dispense 0.5 ml of body wash onto the three middle fingers of the opposite hand (palm side up) in a spiral pattern.

1.4.3. Using your fingers with body wash on them, turn hand downward and scrub the stain for 5 seconds—using 10 circular motions and moderate pressure, at a rate of 2 circular motions per second.

1.5. Rinse the stain 2 times by holding both ends of the fabric (stain side up) and quickly sweeping fabric under running water back and forth (twice).

1.6. Place fabric (stain side up) on paper towel on the counter. Allow to dry overnight.

1.7. Take L,a,b color measurements of dry stain Minolta Chromameter CR300, calculate Delta E vs. untreated stain from same batch of stained fabrics. Delta E=Square Root of (Delta L squared+Delta a squared+Delta b squared).

ii.) Biodegradability

The biodegradability of the skin cleansing composition comprising the biodegradable abrasive particles or the biodegradable abrasive particles can be tested according to the following method. This biodegradability test is based on the Organization for Economic Co-operation and Development (OECD) 301B $CO_2$ evolution biodegradation test method that screens chemicals for ready biodegradability in an aerobic aqueous medium.

In this test the test substance is suspended in a phosphate buffered media containing an activated sludge inoculums and the consumption of oxygen and/or the formation of carbon dioxide is measured via an electrolytic respirometer. The test substance is the sole carbon and energy source and under aerobic conditions microorganisms metabolize organic substances producing $CO_2$ as the ultimate product. The test can run for 28 days or 90 days.

iii.) Yield Stress

The yield stress method employs a TA G2 Rheometer (Stable Micro Systems, Surrey, UK) which is capable of measuring low stress/strain behavior. A steady-state ramp experiment is used in which a sample has a shear stress applied to it starting at a low stress of $10^{-3}$ Pa and slowly ramping up to 100 Pa. Initially, the sample will be displaced, but not at a constant rate—the network undergoes a change due to external forces and requires time to re-establish. Over time, the network will complete this rearrangement under the applied stress and the strain rate/angular velocity will become constant'steady-state conditions are achieved. The rheometer records this angular velocity and ramps up to a higher shear stress and continues the same procedure until the high stress limit as specified in the procedure of 100 Pa. At a certain point, the force applied by the rheometer will approach the force response by the material. When these forces equal, the angular velocity becomes zero. This is determined to be the yield stress of the material network.

Creep is employed using the TA Instruments G2 Rheometer. Geometry of 60 mm plate or 40 mm plate can be used with 1 mm gap (plates). Stress of 0.001, 0.01, 0.10, 1.0, 10.0, 100.0 Pa was applied for up to two hours. Edge effects due to drying are eliminated by using a barrier of 6,000 cst silicone fluid at the sample-air interface, i.e., the plate edge with solvent trap and air baffle also in place. The composition is allowed to rest unstressed for 60 minutes prior to the creep experiment.

Parallel Plate Configuration for Creep Loading and Run Procedure for the G2 Rheometer After mapping, zeroing, etc.:

1. Dispense a slight excess of composition onto the baseplate with no bubbles.
2. Lock upper geometry.
3. Move geometry to 5 microns larger than the desired final gap setting (e.g., 1005 microns).
4. Trim excess fluid and wipe outer top edge surface of top geometry clean; and wipe baseplate edge near the edge of the composition clean carefully with a finger.
5. Using a pipette, drip a curtain of either 10,000 cst dimethicone (DC 200 fluid) or DC1501 fluid (6,000 cst) onto the outer edge of the top geometry in excess so it flows down over the composition and contacts the baseplate, in a complete curtain so no composition is exposed to air.
6. Move geometry to target gap setting.
7. If available, set solvent trap into position for this geometry.
8. Set plexiglass air guard into position.
9. Start measurement.
10. Measurement protocol:
    a. 25.0° C. temperature ('wait for set point'). The supply pump is immersed in a 25° C. cooled water bath to create a constant temperature water supply feed.
    b. 1 minute equilibration prior to start.
    c. Creep step: desired stress into stress field starting at $10^{-3}$ to 100 Pa run for 2 hours at each log of stress.

Exemplary Skin Cleansing Compositions

The following compositions were made by mixing the listed ingredients in the listed proportions (weight %) below. Mixing may be done by devices and techniques known in the art. Examples 1-8 of Table I and Examples 1-4 of Table II herein are meant to exemplify the present invention but are not necessarily used to limit or otherwise define the scope of the present invention.

TABLE 1

| | Examples of Water-Based Body Washes | | | | | | | |
|---|---|---|---|---|---|---|---|---|
| Ingredient | 1 | 2 | 3 | 4 | 5 | 6 | 7 | 8 |
| SLE3S[1] | 6.5 | 6.5 | 7.7 | 7.0 | — | — | 9.1 | 9.1 |
| SLE1S[1] | — | — | — | — | 9.5 | 9.5 | — | — |

TABLE 1-continued

Examples of Water-Based Body Washes

| Ingredient | 1 | 2 | 3 | 4 | 5 | 6 | 7 | 8 |
|---|---|---|---|---|---|---|---|---|
| CAPB[2] | 1.0 | 1.0 | 3.3 | 3.0 | 1.6 | 1.6 | 1.4 | 1.4 |
| SLS[1] | 2.5 | 2.5 | — | — | — | — | — | — |
| NaLaa[3] | — | — | — | — | — | — | 1.0 | 1.0 |
| Trihydroxystearin[4] | 0.5 | 0.3 | 0.5 | 0.3 | 0.5 | 0.3 | — | — |
| Acrylates Copolymer[5] | — | — | — | — | — | — | 1.4 | 1.4 |
| Sodium Benzoate | 0.2 | 0.2 | 0.2 | 0.2 | 0.2 | 0.2 | 0.2 | 0.2 |
| Methylchloroisothiazolinone/ Methylisothiaxolinone[6] | 0.03 | 0.03 | 0.03 | 0.03 | 0.03 | 0.03 | 0.03 | 0.03 |
| Fragrance | 1.0 | 1.1 | 1.1 | 1.25 | 1.25 | 1.25 | 1.13 | 1.0 |
| Disodium EDTA | 0.1 | 0.1 | 0.1 | 0.1 | 0.1 | 0.1 | 0.1 | 0.1 |
| Abrasive particles (PHBV)[7] | 0.2 | — | 0.1 | — | 0.2 | — | 0.1 | — |
| Abrasive particles (PHBV)[8] | — | — | — | 0.2 | — | — | — | 0.3 |
| Abrasive particles (PHBV)[9] | — | 0.2 | — | — | — | 0.2 | — | — |
| Citric Acid | 0.2 | 0.2 | 0.1 | 0.1 | 0.1 | 0.1 | 0.95 | 0.95 |
| NaOH | — | — | — | — | — | — | 0.16 | 0.16 |
| NaCl | 2.0 | 2.0 | 1.5 | 1.5 | 2.0 | 2.0 | 1.7 | 0.75 |
| Dyes/Pigments | — | 0.02 | 0.01 | — | — | 0.02 | 0.2 | 0.2 |
| Water | QS | QS | QS | QS | QS | QS | QS | QS |
| Yield Stress (Pa) | 0.5 | 0.1 | 0.5 | 0.1 | 0.5 | 0.1 | 1.0 | 1.0 |

[1]SLE(n)S where n equals moles of ethoxylation can be obtained from Procter & Gamble, Co., Cincinnati, OH USA.
[2]Cocoamidopropyl Betaine can be obtained from Stepan Corp., Northfield, IL USA.
[3]Sodium Lauroamphoacetate can be obtained from Cogins Chemical Co., Manheim, Germany.
[4]Thixcin ® is the tradename for trihydroxystearin obtained from Elementis Specialties Co., Windsor, NJ USA.
[5]Carbopol Aqua SF-1 ® is the tradename for acrylates copolymer obtained from Lubrizol Corp., Wickliffe, OH USA.
[6]Kathon CG ™ is the tradename available from Rohm & Haas Company, Philadephia, PA USA.
[7]PHBV abrasive particles can be obtained from Tianan Biologic Materials Co., Ningbo, China, particle size of 500 microns with a circularity of 0.4 and a solidity of 0.8.
[8]PHBV abrasive particles can be obtained from Tianan Biologic Materials Co., Ningbo, China, particle size of 1500 microns with a circularity of 0.4 and a solidity of 0.8.
[9]PHBV abrasive particles can be obtained from Tianan Biologic Materials Co., Ningbo, China, particle size of 2000 microns with a circularity of 0.4 and a solidity of 0.8.

TABLE 2

Examples of Lipid-Based Body Washes

| Ingredient | 1 | 2 | 3 | 4 |
|---|---|---|---|---|
| ST3S[1] | 8.5 | 6.3 | — | — |
| ST2S[2] | — | — | 9.3 | 9.3 |
| CAPB[3] | — | — | 2.8 | 2.8 |
| SLS[4] | 8.5 | 6.3 | — | — |
| NaLaa[5] | 5.0 | 3.7 | — | — |
| Trideceth-3 (HLB = 8)[6] | 2.0 | 1.5 | 0.5 | 0.5 |
| Sodium Benzoate | 0.2 | 0.2 | 0.2 | 0.2 |
| Methylchloroisothiazolinone/ Methylisothiaxolinone[7] | 0.05 | 0.05 | 0.03 | 0.03 |
| Fragrance | 1.0 | 0.8 | 1.0 | 1.1 |
| Disodium EDTA | 0.1 | 0.1 | 0.1 | 0.1 |
| Abrasive particles (PHBV)[8] | 0.2 | — | 0.1 | — |
| Abrasive particles (PHBV)[9] | — | 0.1 | — | 0.2 |
| Citric Acid | 0.2 | 0.7 | 0.2 | 0.2 |
| NaCl | 4.8 | 4.0 | 4.8 | 4.8 |
| Dyes | — | 0.01 | 0.02 | — |
| Xanthan Gum[10] | 0.2 | 0.2 | 0.2 | 0.2 |
| PEG-90M Polyox[11] | 0.1 | 0.1 | — | — |
| N-Hance 3196[12] | 0.6 | 0.4 | — | — |
| N-Hance CG-17[12] | — | — | 0.4 | 0.4 |
| Expancel[13] | 0.3 | 0.3 | — | — |
| Aqupec[14] | — | — | 0.05 | 0.05 |
| BHT | — | — | — | 0.1 |
| Petrolatum | 7.0 | 10.5 | 4.9 | — |
| Mineral Oil | — | 4.5 | — | — |
| Glyceryl Monooleate | — | — | 0.1 | 0.1 |
| Water | QS | QS | QS | QS |
| Yield Stress (Pa) | 2 | 1.5 | 1 | 1 |

[1]Sodium Trideceth(n) Sulfate where n = 3 moles ethoxylation can be obtained from Stepan Corp., Northfield, IL USA.
[2]Sodium Trideceth(n) Sulfate where n = 2 moles ethoxylation can be obtained from Stepan Corp., Northfield, IL USA.
[3]Cocoamidopropyl Betaine can be obtained from Stepan Corp., Northfield, IL USA.
[4]Sodium Lauryl Sulfate can be obtained from Procter & Gamble Co., Cincinnati, OH USA.
[5]Sodium Lauroamphoacetatecan be obtained from Cogins Chemical Co., Manheim, Germany.
[6]Iconal TDA-3 ® is available from BASF Corp., Florham Park, NJ USA.
[7]Kathon CG ™ is available from Rohm & Haas Company, Philadephia, PA USA.
[8]PHBV abrasive particles can be obtained from Tianan Biologic Materials Co., Ningbo, China, particle size of 500 microns with a circularity of 0.4 and a solidity of 0.8.
[9]PHBV abrasive particles can be obtained from Tianan Biologic Materials Co., Ningbo, China, particle size of 1500 microns with a circularity of 0.4 and a solidity of 0.8.
[10]Keltrol 1000 ® can be obtained from CP Kelco, Chicago, IL USA.
[11]Polyox WSR-301 ® 90-M, available from Union Carbide Co.
[12]N-Hance ™ polymer series is commercially available from Aqualon, part of Ashland Specialty Co., Covington, KY USA.
[13]Expancel ® is an acrylonitrile/methacrylonitrile/methyl methacrylate copolymer & isopentane obtained from AkzoNobel, Amsterdam, Netherlands
[14]AQUPEC ® SER-300 made by Sumitomo Seika of Tokyo, Japan.

It has been found that shaped particles provide more cleansing than non-shaped particles within a body wash product. Many particles are non-shaped, i.e. have a substantially circular or spherical configuration. Such particles can be easily moved across a surface causing little disruption of stains on a surface, whereas particles that have shape or that are irregular have increased touch points for contact as they are moved across a surface. These shaped particles have increased cleansing ability as shown in Tables 3 and 4 below. A higher ΔE means a higher degree of cleansing.

TABLE 3

Cleansing Efficiency (Example One)

| Sample | L-value | a-value | b-value | ΔE |
|---|---|---|---|---|
| Stain #1 (Initial Value) | 56.31 | 3.40 | 11.45 | n/a |
| Body Wash with No Particles (Control) | 59.37 | 3.52 | 12.44 | 3 |
| Body Wash with Shaped Particles | 67.60 | 1.70 | 10.61 | 11 |
| Body Wash with Non-Shaped Particles | 64.44 | 2.79 | 11.11 | 8 |

TABLE 4

Cleansing Efficiency (Example Two)

| Sample | L-value | a-value | b-value | ΔE |
|---|---|---|---|---|
| Stain #2 (Initial Value) | 50.21 | 2.62 | 9.30 | n/a |
| Body Wash with No Particles (Control) | 53.86 | 3.63 | 11.11 | 4 |
| Body Wash with Shaped Particles | 61.62 | 2.39 | 10.78 | 12 |
| Body Wash with Non-Shaped Particles | 57.56 | 3.32 | 11.19 | 8 |

As shown in Tables 3 and 4, a body wash product containing shaped particles has a larger ΔE compared to non-shaped particles. The same lipid-based product was used as the chassis for each body wash test product. Both body wash products containing particles have more cleaning (higher ΔE) than a control body wash product with no particles. The data shows a significant difference between shaped (ΔE~12) and non-shaped particles (ΔE~8). A difference of ΔE=4 has been shown to be a significant difference based on consumer testing. The particles have a particle size of between 840 to 1400 μm with a circularity of 0.4 and a solidity of 0.8. The non shaped particles have a Circularity of around 0.9-1.

TABLE 5

Examples of Bar Soaps

| Material | Ex1A | Ex1B | Ex2A | Ex2B |
|---|---|---|---|---|
| Na Cocoyl Isethionate | 19.58 | 19.58 | — | — |
| Na Topped Cocoyl Isethionate | — | — | 19.58 | 19.58 |
| Na Alkyl Glyceryl Ether Sulfonate | 19.58 | 19.58 | 19.58 | 19.58 |
| Polyethylene Glycol Polymer (1) | 0.025 | 0.025 | 0.025 | 0.025 |
| Sodium Soap | 9.7 | 9.7 | 9.7 | 9.7 |
| Magnesium Soap | 3.73 | 3.73 | 3.73 | 3.73 |
| Free Fatty Acid (STCI) | 0.13 | 0.13 | 0.13 | 0.13 |
| Paraffin High Melt Point (~70° C.) | 27.42 | 27.42 | 27.42 | 27.42 |
| NaCl | 0.67 | 0.67 | 0.67 | 0.67 |
| $Na_2SO_4$ | 1.12 | 1.12 | 1.12 | 1.12 |
| Sodium Isethionate | 1.12 | 1.12 | 1.12 | 1.12 |
| Glycerin | 3.70 | 3.70 | 3.70 | 3.70 |
| Water | 5.80 | 5.80 | 5.80 | 5.80 |
| PHBV (2) | 0.20 | — | 0.20 | — |
| PHBV (3) | — | 0.20 | — | 0.20 |
| Fragrance | 1.00 | 1.00 | 1.00 | 1.00 |
| Palmitic Acid | 0.15 | 0.15 | 0.15 | 0.15 |
| Myristic Acid | 0.15 | 0.15 | 0.15 | 0.15 |
| $TiO_2$ | 0.35 | 0.35 | 0.35 | 0.35 |
| Trisodium EDTA | 0.10 | 0.10 | 0.10 | 0.10 |
| Trisodium Etidronate | 0.10 | 0.10 | 0.10 | 0.10 |
| Minors (4) | Balance | Balance | Balance | Balance |

(1) Polyox WSR-301 ® 90-M, available from Union Carbide Co.
(2) PHBV abrasive particles can be obtained from Tianan Biologic Materials Co., Ningbo, China, particle size of 500 microns with a circularity of 0.4 and a solidity of 0.8.
(3) PHBV abrasive particles can be obtained from Tianan Biologic Materials Co., Ningbo, China, particle size of 1500 microns with a circularity of 0.4 and a solidity of 0.8.
(4) Minors include unreacted feedstocks and products of secondary side rections.

The bars of Table 5 may be made according to U.S. Pat. No. 5,945,389, Richard et al., which is herein incorporated by reference.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A skin cleansing composition comprising:
   a. from about 0.1% to about 10% or from about 0.1% to about 1% by weight of the composition, of biodegradable abrasive particles comprising:
      i. a mean Circularity of from about 0.10 to about 0.60, or from about 0.15 to about 0.55, according to ISO 9276-6:2008;
      ii. a mean particle size as expressed by the area-equivalent diameter from about 850 μm to about 2000 μm, according to ISO 9276-6:2008;
      iii. a Biodegradable Rate of about 30% to about 100% or from about 40% to about 95%, as determined after 28 days according to the Biodegradability Test;
      iv. a hardness of from about 35 to about 75, according to ASTM D2240-05-2010;
   b. a surfactant phase selected from the group consisting of b(i) or b(ii);
      i. a structured surfactant phase comprising:
         1. from about 5% to about 20% or from about 5% to about 10% by weight of the composition, of a surfactant selected from the group consisting of STnS where n is between about 0 and about 3 or from about 0.5 to about 3 or from about 1.1 to about 3, isethionates, glycinates, succinates, glucosides, amphoacetates, ethanolamines, glutamates, taurates, betaines, phosphates, sarcosinates, sultaines, sulfonates, and combinations thereof;
         2. optionally from about 0% to about 10% of SLS;
         3. a structuring system comprising from about 0.05% to about 10% or from about 0.5% to about 5% by weight, of an electrolyte; and optionally from about 0.05% to about 0.5% of an associative polymer;
      wherein the composition has a Yield Stress of about 1 Pa to about 100 Pa;
      ii. a surfactant phase comprising:
         1. from about 5% to about 20% or from about 5% to about 14% by weight of the composition, of a surfactant selected from the group consisting of SLEnS where n is about 0 to about 3, isethionates, glycinates, succinates, glucosides, amphoacetates, ethanolamines, glutamates, taurates, betaines, phosphates, sarcosinates, sultaines, sulfonates, and combinations thereof;
         2. optionally from about 0% to about 10% of SLS;

3. from about 0.05% to about 5% by weight, of an electrolyte, and
4. a structuring system comprising from about 0.05% to about 5% or about 0.05% to about 1% by weight of the composition, of a structuring material selected from the group consisting of an associative polymer, trihydroxystearin or combinations thereof;

wherein the composition has a Yield Stress of about 0.1 Pa to about 10 Pa.

2. The skin cleansing composition according to claim 1, wherein the Yield Stress for b(i) is from about 1 Pa to about 10 Pa and the Yield Stress for b(ii) is from about 0.1 Pa to about 1 Pa.

3. The skin cleansing composition according to claim 1, the abrasive particles further comprising a mean Solidity from about 0.60, 0.65, 0.70, or 0.75 to about 0.80, 0.90, 0.95, or 1.0, according to ISO 9276-6:2008.

4. The skin cleansing composition according to claim 1, wherein the skin cleansing composition has a Biodegradable Rate of from about 60%, or about 70%, to about 90% or 100%, after 28 days according to the Biodegradability Test.

5. The skin cleansing composition according to claim 1, wherein the abrasive particles are selected from the group of polymeric material consisting of:
(a) one or more homo-polymers or co-polymers selected from the group consisting of polyhydroxy alkanoate (PHA), polylactic acid derivatives (PLA), polycaprolactone (PLC), poly(glycolic acid) (PGA), and blends thereof;
(b) aliphatic or, aromatic co-polyesters, selected from co-polyester containing succinic, glutaric, adipic, terepthalic diacids, propanediol, butanediol, pentanediol, hexanediol monomer or blends thereof;
(c) starch, thermoplastic starch (TPS), or blends thereof;
(d) thermoplastic cellulose (TPC) derivative selected from the group consisting of cellulose ester, cellulose ether, cellulose alkanoate and blends thereof; and
(e) combinations of (a) to (d).

6. The skin cleansing composition according to claim 5, wherein the polymeric material is polyhydroxy alkanoate (PHA) selected from the group consisting of poly-3-hydroxybutyrate (PHB), poly-3-hydroxyhexanoate, poly-3-hydroxy-valerate, poly-3-hydroxy-butyrate-co-3-hydroxyvalerate (PHBV), poly-3-hydroxybutyrate-co-3-hydroxyhexanoate, and blends thereof.

7. The skin cleansing composition according to claim 6, wherein the polymeric material is poly-3-hydroxy-butyrate-co-3-hydroxyvalerate (PHBV).

8. The skin cleansing composition according to claim 1, wherein the surfactant phase is b(ii) and is an aqueous surfactant phase; the surfactant is SLEnS where n is 0 to about 3; the structuring material is selected from the group consisting of an alkyl acrylate polymer, trihydroxystrearin, and combinations thereof; and the electrolyte comprises an anion selected from the group consisting of phosphate, chloride, sulfate, citrate, and mixtures thereof, and a cation selected from the group consisting of sodium, ammonium, potassium, magnesium, and mixtures thereof.

9. The composition according to claim 8, wherein the electrolyte is selected from the group consisting of sodium chloride, ammonium chloride, sodium sulfate, ammonium sulfate, and mixtures thereof.

10. The composition according to claim 1, wherein the structured surfactant phase is b(i); the surfactant is STnS where n is from about 0.5 to about 3; the structuring system comprises an electrolyte and an associative polymer that is alkyl acrylate polymer; the electrolyte comprises an anion selected from the group consisting of phosphate, chloride, sulfate, citrate, and mixtures thereof, and a cation selected from the group consisting of sodium, ammonium, potassium, magnesium, and mixtures thereof.

11. The composition according to claim 10, wherein the electrolyte is selected from the group consisting of sodium chloride, ammonium chloride, sodium sulfate, ammonium sulfate, and mixtures thereof.

12. The composition according to claim 10, wherein the associative polymer is selected from the group consisting of polyacrylates, hydrophobically modified polysaccharides, hydrophobically modified urethanes, and/or mixtures thereof.

13. The composition according to claim 12, wherein the associative polymer comprises an alkyl acrylate polymer.

14. The skin cleansing composition according to claim 10, wherein the structuring system for b(i) further comprises from about 0.01% to about 5% or 0.1% to about 0.03%, by weight of a non-associative polymer selected from the group consisting of polysaccharides, synthetic hydrocarbon polymers, and combinations thereof.

15. The skin cleansing composition according to claim 1, the skin cleansing composition has a viscosity from about 100 cps to about 1,000,000 cps, or from about 1,000 cps to about 300,000 cps, or from about 5,000 cps to about 200,000 cps.

16. The skin cleansing composition according to claim 1, wherein the skin cleansing composition has a pH of about 5 to about 8 or about 5.5 to about 6.5.

17. The skin cleansing composition according to claim 1, wherein the skin cleansing composition further comprises one or more actives selected from the group consisting of sugar amines, vitamins, oil control agents, phytosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratine protecting agents, emollients, moisturizers, and combinations thereof.

18. A method for cleansing a human's skin surface comprising contacting the skin surface with a skin cleansing composition according to claim 1, and additionally followed by a rinsing step.

* * * * *